(12) United States Patent
Yang et al.

(10) Patent No.: US 10,413,181 B2
(45) Date of Patent: Sep. 17, 2019

(54) HEAD HEALTH CARE DEVICE AND HEAD HEALTH CARE SYSTEM

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Shengji Yang, Beijing (CN); Xue Dong, Beijing (CN); Hailin Xue, Beijing (CN); Haisheng Wang, Beijing (CN); Xiaochuan Chen, Beijing (CN); Yingming Liu, Beijing (CN); Weijie Zhao, Beijing (CN); Xiaoliang Ding, Beijing (CN); Lei Wang, Beijing (CN); Rui Xu, Beijing (CN); Changfeng Li, Beijing (CN); Wei Liu, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 178 days.

(21) Appl. No.: 15/518,411

(22) PCT Filed: Dec. 31, 2015

(86) PCT No.: PCT/CN2015/100134
§ 371 (c)(1),
(2) Date: Apr. 11, 2017

(87) PCT Pub. No.: WO2017/036046
PCT Pub. Date: Mar. 9, 2017

(65) Prior Publication Data
US 2017/0303783 A1    Oct. 26, 2017

(30) Foreign Application Priority Data

Aug. 28, 2015    (CN) .......................... 2015 1 0539739

(51) Int. Cl.
*A46B 11/04*        (2006.01)
*A61B 5/00*         (2006.01)
(Continued)

(52) U.S. Cl.
CPC ............... *A61B 5/00* (2013.01); *A46B 9/023* (2013.01); *A46B 11/001* (2013.01);
(Continued)

(58) Field of Classification Search
CPC ............ A46B 2200/102; A46B 11/002; A46B 11/0006; A61B 5/442; A62B 5/445
See application file for complete search history.

(56) References Cited

U.S. PATENT DOCUMENTS

| | | |
|---|---|---|
| 4,877,042 A | 10/1989 | Downey |
| 2005/0120779 A1 | 6/2005 | Sherman et al. |

(Continued)

FOREIGN PATENT DOCUMENTS

| | | |
|---|---|---|
| CN | 1375250 A | 10/2002 |
| CN | 1662812 A | 8/2005 |

(Continued)

OTHER PUBLICATIONS

The First Chinese Office Action dated Jul. 1, 2016; Appln. No. 201510539739.4.

(Continued)

*Primary Examiner* — Jennifer C Chiang
(74) *Attorney, Agent, or Firm* — Ladas & Parry LLP

(57) ABSTRACT

A head health care device and a head care system are provided. The head health care device includes: a body; a plurality of sensing components provided and projected on (Continued)

an outer surface of the body, in which each sensing component is configured to sense head information of a user; and a plurality of health care components provided and projected on the outer surface of the body, in which the health care components are configured to perform health care operations on a head of the user according to a control signal.

18 Claims, 3 Drawing Sheets

(51) Int. Cl.
*A61M 35/00* (2006.01)
*A46B 11/00* (2006.01)
*A46B 9/02* (2006.01)
*A46B 15/00* (2006.01)

(52) U.S. Cl.
CPC .......... *A46B 15/0022* (2013.01); *A61B 5/443* (2013.01); *A61B 5/445* (2013.01); *A61B 5/4839* (2013.01); *A61M 35/00* (2013.01); *A61B 2560/0468* (2013.01); *A61B 2562/02* (2013.01)

(56) References Cited

U.S. PATENT DOCUMENTS

| 2008/0125835 | A1 | 5/2008 | Laurent |
| 2010/0139682 | A1* | 6/2010 | Edgar ................. A45D 19/02 132/208 |
| 2010/0224205 | A1 | 9/2010 | Mitra et al. |
| 2015/0265025 | A1* | 9/2015 | Alsalameh ............ A45D 24/22 132/113 |
| 2015/0342515 | A1* | 12/2015 | Hutchings ............. A45D 24/00 132/200 |

FOREIGN PATENT DOCUMENTS

| CN | 201700628 U | 1/2011 |
| CN | 103251199 A | 8/2013 |
| CN | 105167749 A | 12/2015 |
| CN | 204950901 U | 1/2016 |
| GB | 2147204 A | 5/1985 |
| JP | 2005-218522 A | 8/2018 |
| KR | 20020014622 A | 2/2002 |

OTHER PUBLICATIONS

The Second Chinese Office Action dated Dec. 2, 2016; Appln. No. 201510539739.4.
The International Search Report and Written Opinion dated May 20, 2016; PCT/CN2015/100134.
Extended European Search Report dated Apr. 8, 2019; Appln. No. 15902850.5.

* cited by examiner

HEAD HEALTH CARE DEVICE AND HEAD HEALTH CARE SYSTEM

TECHNICAL FIELD

Embodiments of the present disclosure relate to a head health care device and a health care system corresponding to the head health care device.

BACKGROUND

Smart household appliances are household appliances formed by incorporation of microprocessor technology, sensor technology and network communication technology into home appliances, and have automatic sensing function and remote control function. In recent years, smart household appliances have gradually entered tens of thousands of households, and various kinds of smart household appliances are integrated with more high-tech features, and bring convenience to users while promoting the development of science and technology.

With the continuous improvement of living standards, people pay more and more attention to hair and head care, and many people want to choose different health care means and care ways according to own head conditions. But users often need professional knowledge to determine the hair quality of their own hair and choose proper care ways. It is very cumbersome and difficult to common users. Therefore, users hope to search for a smart household appliance solution.

SUMMARY

An embodiment of the present disclosure provides a head health care device, comprising: a body; a plurality of sensing components provided and projected on an outer surface of the body, in which each sensing component is configured to sense head information of a user; and a plurality of health care components provided and projected on the outer surface of the body, in which the health care components are configured to perform health care operations on a head of the user according to a control signal.

For example, at least one sensing component includes a sensing signal output part; at least one sensing component includes a sensing signal receiving part; the sensing signal output part is configured to send out a sensing drive signal; and the sensing signal receiving part is configured to receive a sensing signal.

For example, a number of the sensing components each including the sensing signal receiving part is greater than a number of the sensing components each including the sensing signal output part; and sensing components each including the sensing signal receiving part are distributed around the sensing components each including the sensing signal output part.

For example, the body is internally provided with a cavity with a limited space; the cavity is provided with a nutrient solution storage tank; and the nutrient solution storage tank is configured to output nutrient solution to the health care components according to the control signal and allow the nutrient solution to be discharged.

For example, the nutrient solution storage tank includes a plurality of vessels; the vessels are respectively configured to store different types of nutrient solutions, and at least one type of nutrient solution in the vessels can be conveyed to one corresponding health care component according to an instruction of the control signal and discharged.

For example, the health care device further comprises a nutrient solution storage tank driver; and the nutrient solution storage tank driver is configured to drive the nutrient solution storage tank to output the nutrient solution to the health care components according to the control signal.

For example, the health care device further comprises a controller; and the controller is disposed in the body and configured to generate the control signal according to information sensed by the sensing components, and send the control signal to the health care components to control the health care operations of the health care components.

For example, the controller further includes a sensing signal transmitting terminal and a sensing signal receiving terminal; the sensing signal transmitting terminal is configured to provide the sensing drive signal to the sensing signal output part of the sensing component; and the sensing signal receiving terminal is configured to receive the sensing signal from the sensing signal receiving part of the sensing component.

For example, the health care device further comprises a vibrating component; and the vibrating component drives at least one health care component to vibrate according to the control signal.

For example, the health care device is in a shape of a comb; and the sensing components and the health care components are disposed on comb teeth of the comb.

For example, one health care component and one sensing component are disposed on a same comb tooth.

For example, the health care device further comprises an information storage device.

For example, the health care device further comprises a signal transmitting/receiving device; and the signal transmitting/receiving device is configured to communicate with an external device and receive the control signal.

For example, the health care device further comprises a plurality of function buttons.

For example, the health care device further comprises a built-in power supply or a power port.

For example, the health care device further comprises an input/output device.

Another embodiment of the present disclosure provides a head health care system, comprising the head health care device; and a controller configured to communicate with the head health care device, wherein the head health care device is configured to send the head information of the user sensed by the sensing components to the controller; and the controller is configured to generate the control signal according to the received head information of the user, and send the control signal to the health care components to control the health care operations of the health care components.

For example, the controller further includes a sensing signal transmitting terminal and a sensing signal receiving terminal; the sensing signal transmitting terminal is configured to provide the sensing drive signal to the sensing signal output part of the sensing component; and the sensing signal receiving terminal is configured to receive the sensing signal from the sensing signal receiving part of the sensing component.

For example, the system further comprises an input/output device; the input/output device is configured to receive information inputted by the user; and the controller also generates the control signal according to the information inputted by the user.

For example, the controller is a mobile terminal configured to communicate with the head health care device.

BRIEF DESCRIPTION OF THE DRAWINGS

In order to clearly illustrate the technical solution of the embodiments of the disclosure, the drawings of the embodiments will be briefly described in the following; it is obvious that the described drawings are only related to some embodiments of the disclosure and thus are not limitative of the disclosure.

REFERENCE NUMERALS

100: head health care device;
110: body;
120: sensing component;
130: health care component;
111: cavity;
112: nutrient solution storage tank;
1121: vessel;
1122: vessel;
1123: vessel;
121: sensing signal output part;
122: sensing signal receiving part;
113: nutrient solution storage tank driver;
140: controller;
150: handle;
160: button;
170: vibrating component;
141: information storage device;
190: signal transmitting/receiving device;
180: input/output device;
300: head health care system;
310: head health care device;
311: sensing component;
312: health care component;
320: controller.

DETAILED DESCRIPTION

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Figure 1A:
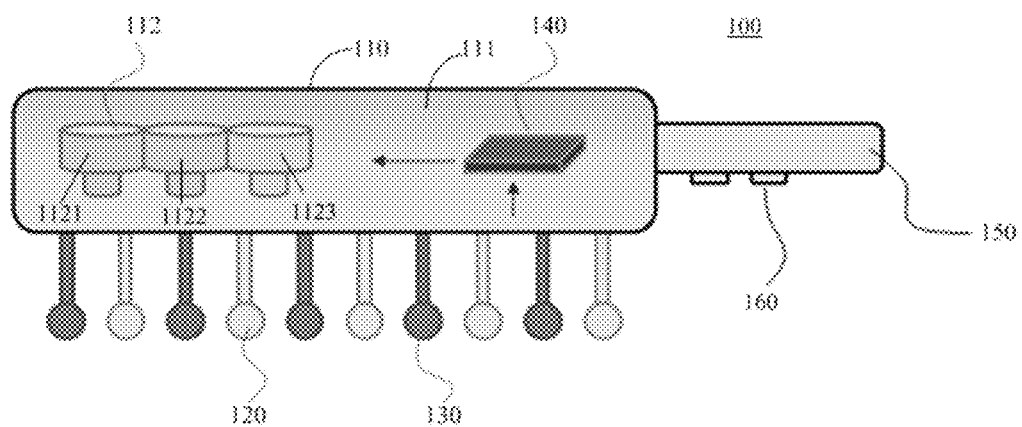
FIGS. 1a, 1b and 1c are schematic structural views of a head health care device provided by an embodiment of the present disclosure.
Figure 1B:
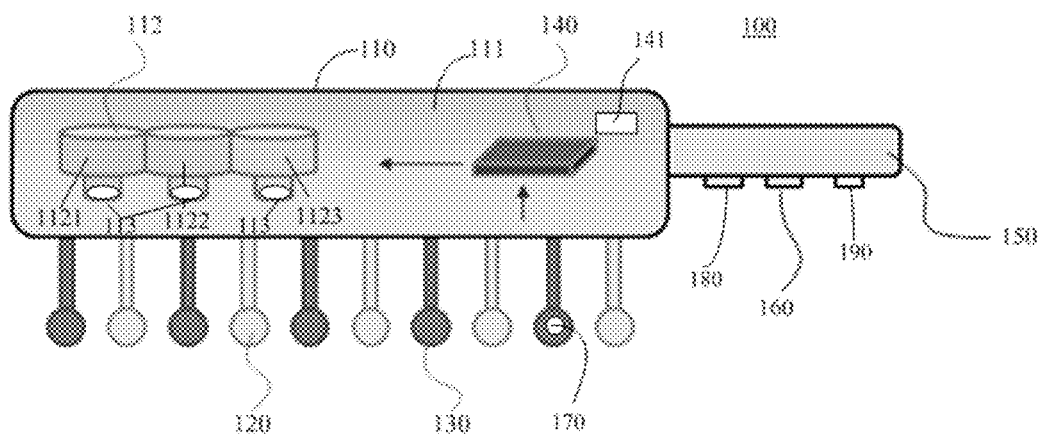

FIG. 1 is a schematic diagram of a head health care device provided by an embodiment of the present disclosure. Description will be given below to the structure, functions and operation mode of the head health care device provided by the embodiment of the present disclosure with reference to FIG. 1.

As illustrated in FIG. 1, a head health care device 100 provided by one embodiment of the present disclosure comprises: a body 110, sensing components 120, and health care components 130.

The body 110 is a main part of the head health care device 100, is a solid body or a hollow body with a certain external shape, and may be made from a plastic, a metal or another material.

One or more sensing components 120 may be provided and are projected on an outer surface of the body 110. Each sensing component 120 is configured to sense head information of a user. The head information, for instance, may be hair quality information of the hair of the user (e.g., oily, dry or neutral hair), head nutrition information of the user (e.g., undernutrition or overnutrition), head cleanliness information of the user, head physiologic information of the user (e.g., blood circulation condition), or the like.

One or more health care components 130 may be provided and are also projected on the outer surface of the body 110 the same as the sensing components 120. Each of the health care component 130 is configured to perform health care operation on the head of the user as required under the control of the head health care device. The health care operation, for instance, may be nutrient solution supply, massage, cleaning, humidifying, drying or the like.

Detailed description will be given below to the structures and/or operation modes of the above three main components.

FIG. 1 is a schematic structural view of the head health care device 100 provided by one embodiment of the present disclosure. As illustrated in FIG. 1, according to one example of the present disclosure, the body 110 is internally provided with a cavity 111 with a limited space; the cavity 111 is provided therein with a nutrient solution storage tank 112; and the nutrient solution storage tank 112 may output nutrient solution to the health care component(s) 130 under the control of the head health care device, and then the nutrient solution may be discharged to, for instance, the scalp position of the user, by the health care components 130. For instance, the nutrient solution storage tank 112 includes a plurality of vessels 1121, 1122 and 1123, and each vessel stores different types of nutrient solutions. For instance, the vessels respectively store dry hair nutrient solution, neutral hair nutrient solution and oily hair nutrient solution, and the nutrient solutions can be prepared as required or purchased from the market. Optionally, the body 110 may include a nutrient solution storage tank driver or drivers 113. When receiving a control instruction for outputting the nutrient solution of the head health care device, the nutrient solution storage tank driver(s) 113 may convey at least one nutrient solution in the vessels 1121, 1122 and 1123 of the nutrient solution storage tank 112 to the health care component(s) 130, and then the nutrient solution is discharged by the health care component(s) 130. For instance, the nutrient solution storage tank driver may be communicated with one valve switch on the vessel, and controls the output of the nutrient solution by switching on and off the valve according to the control instruction of the head health care device. The nutrient solution may be discharged by extruding the nutrient solution storage tank or injecting gas into the nutrient solution storage tank.

Figure 1C:
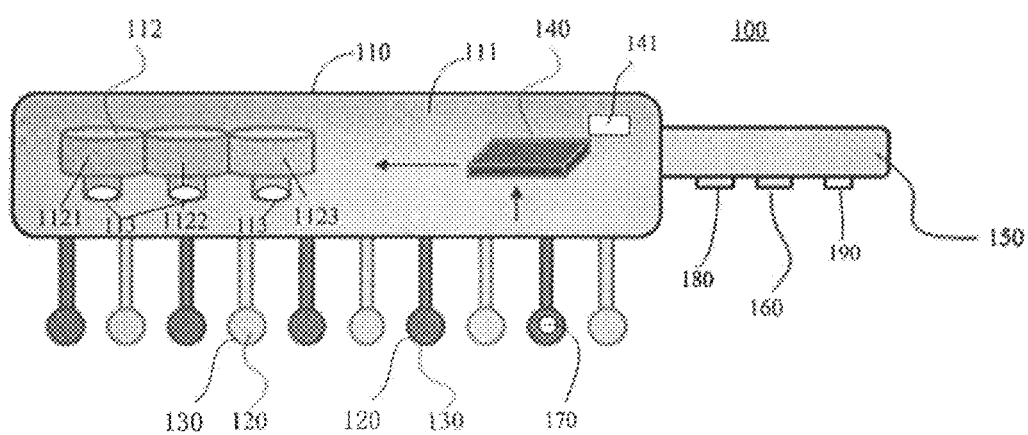
Figure 2:
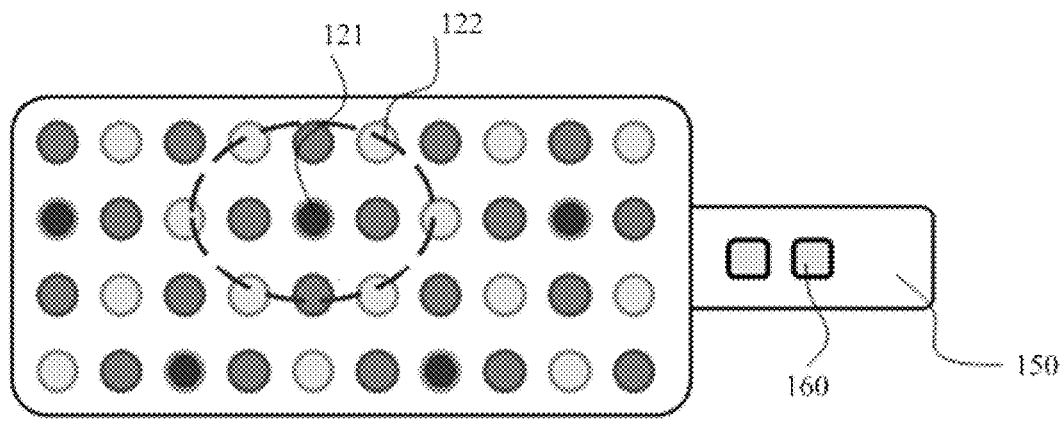
FIG. 2 is a schematic structural view of sensing components in an embodiment of the present disclosure.

FIG. 2 is a schematic structural view of the sensing components 120 and is also a bottom view of FIG. 1. As illustrated in FIG. 2, according to one example of the present disclosure, the sensing components 120 include sensing signal output parts 121 and sensing signal receiving parts 122. When the head health care device 100 comprises one sensing component 120, the sensing component 120 may simultaneously include a sensing signal output part 121 and a sensing signal receiving part 122. When the head health care device 100 comprises a plurality of sensing components 120, at least one sensing component 120 includes a sensing signal output part 121, and at least one sensing component 120 includes a sensing signal receiving part 122. The sensing signal output part 121 can send out a sensing drive signal, and the sensing signal receiving part 122 can receive a sensing signal. The sensing signal output part 121, for instance, may be a sensing output probe, and the sensing signal receiving part 122, for instance, may be a sensing receiving probe.

In an embodiment of the present disclosure, the sensing components 120 may be sensors with a specific function(s), e.g., biosensors, capacitive sensors, or the like. A positive electrode is disposed on the sensing signal output part 121, and a negative electrode is disposed on the sensing signal receiving part 122. When the sensing signal output part 121 and the sensing signal receiving part 122 respectively make contact with any two different positions of the head skin or the hair of the user, as substances (for instance, enzymes, cells, proteins, microorganisms, etc.) contained in human organism and body fluid can conduct electricity, the sensing drive signal transmitted by the sensing signal output part 121 may be transferred to the sensing signal receiving part 122 through the head organism or the body fluid of the user. At this point, the positive and negative electrodes are conducted, and the sensing components may start the sensing operation to detect the hair quality and the nutrition condition of the user.

Optionally, when the sensing component 120 is a capacitive sensor, a detector in the sensing component can detect the specific inductive capacity (SIC) of the head skin and the hair of the user according to capacitance variation. As different hair qualities or skins have different SIC values, the hair quality information of the user can be acquired according to the detected SIC. Whether the hair is oil, neutral or dry may be further determined according to the hair quality information. Different health care operations may be performed according to the hair quality.

Optionally, when the sensing component 120 is a biosensor, a detector in the sensing component, for instance, includes an electrical scanner which may acquire information relevant to ECG changes such as pulse on the head of the user. As different ECG changes may reflect the emotion, the active state and other conditions of the user, the emotional state information of the user may be acquired according to the detected information. For instance, whether the user is in a sleep state or an active state or whether the user is gentle or excited may be determined, and then different health care operations are performed according to the different states.

The above types of sensors are only illustrative, but the present disclosure is not limited thereto. It should be understood by those skilled in the art that the sensing components may also be various other types of sensors. For instance, a temperature sensor is configured to sense the body temperature of the head of the user; a humidity sensor is configured to sense the humidity of the head; and different health care operations are performed according to the sensing results of different sensors.

According to one example of the present disclosure, in the sensing components 120, the number of the sensing components that include the sensing signal receiving parts 122 may be greater than the number of the sensing components that include the sensing signal output parts 121. As illustrated in FIG. 2, a plurality of sensing components 120 including the sensing signal receiving parts 122 (namely the plurality of components connected by dotted lines) are distributed around the sensing component 120 including the sensing signal output part 121. After the sensing signal output part 121 transmits the sensing drive signal, the signal may be transmitted towards various directions and positions of the head of the user. Thus, one or several sensing signal output parts 121 can be utilized to output the sensing drive signal(s), and more sensing signal receiving parts 122 can be utilized to receive the sensing drive signal(s). Therefore, the information about the head skin and the hair of the user can be fully sensed and acquired at a position(s) which the head health care device is in contact with.

In an embodiment of the present disclosure, the health care component 130 may include a variety of elements having health care function. According to one example of the embodiment of the present disclosure, the health care component 130 may be a massager having massage function; after the sensing components 120 determine that the user needs head massage according to the detected information such as emotion, condition and hair quality of the user, the information is transmitted to the health care components 130, and the health care components 130 can massage the head under the control of the control signal. Optionally, the head health care device comprises a vibrating component 170 (e.g., a vibrating motor). For instance, the vibrating component 170 can drive at least one health care component 130 to vibrate under the control of the head health care device.

According to another example of the present disclosure, the health care component 130 may also include a nutrient solution output unit. When the sensing components 120 detect that the head of the user needs a certain kind of nutrition, the information can be transmitted to the health care components 130, and the health care components 130 will convey the nutrient solution to the head of the user according to the information and apply nutrition onto the head. For instance, in FIG. 1, the comb-shaped health care components 130 may be designed to be hollow components; and under the control of the head health care device, the health care components 130 can convey and discharge the nutrient solution in the nutrient solution storage tank 112 onto the head of the user.

According to still another example of the present disclosure, the health care component 130 may also include a dryer. When the sensing components 120 detect that the head humidity of the user exceeds a threshold value, the information can be transmitted to the health care components 130, and the health care components 130 automatically turns on the drying function according to the information to dry the hair of the user; blow-out airflow is, for instance, outputted from holes formed on the health care components 130; and moreover, for instance, the blow-out airflow may further be heated as required.

The above examples of the health care components 130 are only illustrative. It should be understood by those skilled in the art that the health care components 130 may be other components having health care and maintenance functions. For instance, the health care components 130 may also be humidifiers, cleaners, etc.

According to one example of the present disclosure, the head health care device may further comprise a controller 140. The controller 140 may be disposed in the body 110. For instance, in FIG. 1, the controller 140 is disposed in the cavity 111 of the body 110. Of course, it should be understood by those skilled in the art that the controller 140 may also be disposed outside of the body 110. For instance, the controller 140 may be disposed above or below the body, or the controller 140 may be an external device which is completely separated from the head health care device and communicated with the head health care device by wired or wireless means (e.g., wireless local area network (WLAN) and Bluetooth). After the head health care device is turned on, the controller 140 may send the sensing drive signal to the sensing components 120, generate a control signal according to information sensed by the sensing components 120, and then send the control signal to the health care components 130 to control the health care operations of the health care components. The controller 140, for instance, may be achieved by a microprocessor chip, a digital processor or the like mounted in the head health care device.

Optionally, the controller 140 includes a sensing signal transmitting terminal and a sensing signal receiving terminal. During operation, the sensing signal transmitting terminal of the controller 140 is configured to provide the sensing drive signal to the sensing signal output part 121 of the sensing component 120, and the sensing signal receiving terminal is configured to receive the sensing signal from the sensing signal receiving part 122 of the sensing component 120.

According to one example of the present disclosure, the head health care device may be in the shape of a comb, and then has the function of a comb as well. For instance, both the sensing components 120 and the health care components 130 are disposed on comb teeth of the comb. When the head health care device is not energized, the head health care device may be used as a common comb. When the head health care device is energized and turned on, the sensing components 120 and the health care components 130 on the comb teeth of the head health care device enter working states. If the user combs the hair at this point, when the comb teeth make contact with the head skin or the hair of the user, the sensing components disposed in the comb teeth can detect head information; and the health care components will vibrate, apply nutrient solution or conduct other health care operations. Optionally, as shown in FIG. 1c, one health care component 130 and one sensing component 120 may be provided on same one comb tooth. For instance, the tail end of one comb tooth or the tail ends of a plurality of comb teeth are not only provided with the sensing components but also provided with the health care components.

In addition, as a smart household appliance, the head health care device may also comprise an information storage device 141 (e.g., a nonvolatile memory, a flash memory, or the like) which is configured to store the head information of the user sensed by the sensing components 120, or to store the usage habits of the user in which case, at each usage, the health care operation can be directly performed according to the stored information without the detection of the sensing components 120. Optionally, in an embodiment of the present disclosure, the head health care device may be connected with an external device, e.g., a mobile terminal. The mobile terminal is, for instance, a mobile phone, a tablet PC or a host controller. The host controller is, for instance, an intelligent router. For instance, the mobile phone or the tablet PC may be provided with corresponding applications (Apps) to acquire and display information, send an instruction, etc. The head health care device provided by an embodiment of the present disclosure may comprise an input/output device 180 and a signal transmitting/receiving device 190. The signal transmitting/receiving device 190 is communicated with the external device and configured to receive the control signal. The input/output device 180, for instance, may receive an input operation of the user and feed back information to the user through an output unit (e.g., an indicator lamp or a display), and the user may examine and know his/her own hair quality or nutrition condition at any time. In addition, the head health care device may further comprise a handle 150 which is helpful for the user to hold the head health care device, or may comprise a function button(s) 160 which facilitates the operation of the health care device by the user. In an embodiment of the present disclosure, the head health care device may further comprise a built-in power supply or a power port, and power is supplied by a built-in battery or an external DC or AC power supply.

An embodiment of the present disclosure senses the head information of the user through the sensing components and performs corresponding health care operation according to the sensed information, can achieve the health care and maintenance of the head in the case that the user does not need to know and analyze own head information, and hence expands the functions of the conventional health care device and the function of comb, realizes intelligentized head health care, and facilitates the use of the user.

Another embodiment of the present disclosure provides a head health care system. The system is at least partially based on the first embodiment. The difference is only in that the controller in the first embodiment is disposed in the head health care device but the embodiment comprises a controller which is disposed outside of a head health care device and can be connected and communicated with the head health care device. In an embodiment, for instance, the head health care device may further comprise another controller, and the controller may cooperate with the external controller for better control for the operations of the head health care device. Only brief description will be given below for the brevity of the description.

Figure 3:
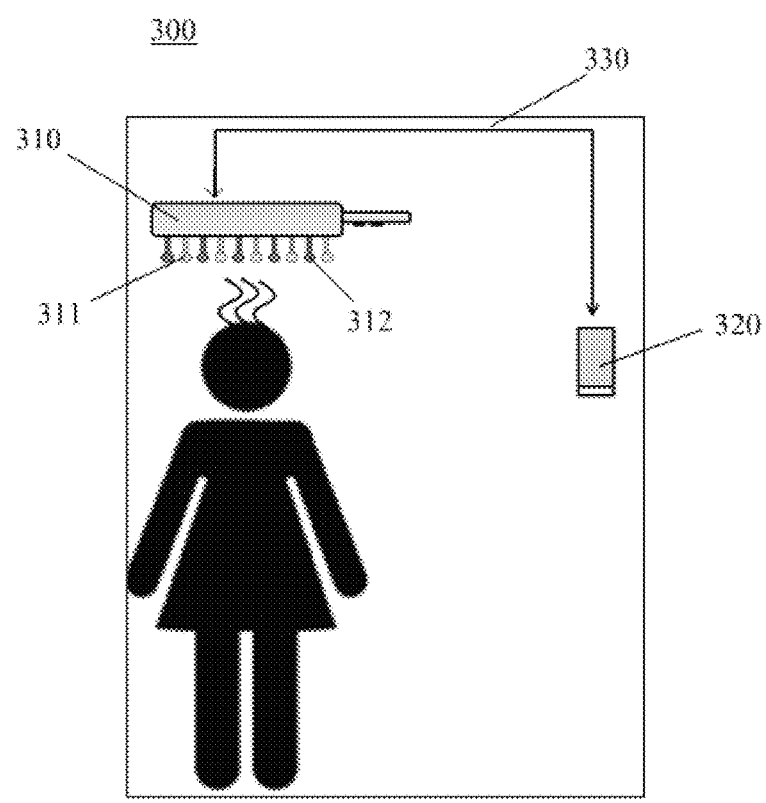
FIG. 3 is an architecture diagram of a head health care system provided by an embodiment of the present disclosure.

FIG. 3 is an architecture diagram of the head health care system provided by an embodiment of the present disclosure. As illustrated in FIG. 3, the system 300 comprises a head health care device 310 and a controller 320. The head health care device 310 sends head information of a user sensed by sensing components 311 to the controller 320 communicated with the head health care device through a communication medium 330, and the controller 320 generates a control signal according to the received head information of the user, and sends the control signal to health care components 312 through the communication medium 330, so as to control the health care operations of the health care components 312. According to one example of the present disclosure, the controller 320 may be provided as an electronic device such as a mobile terminal (e.g., a mobile phone or a tablet PC), a portable computer and a game machine, or software, hardware or firmware having processing and control functions in any of the above devices. The communication medium 330, for instance, may be a wired communication medium, a wireless communication medium (e.g., Wireless Fidelity (WIFI). Bluetooth or a mobile communication network), an infrared transmission medium, etc.

Optionally, the controller 320 further includes sensing signal transmitting terminals and sensing signal receiving terminals. During operation, the sensing signal transmitting terminal is configured to provide a sensing drive signal to a sensing signal output part of the sensing component, and the sensing signal receiving terminal is configured to receive a sensing signal from a sensing signal receiving part of the sensing component.

Optionally, the head health care system 300 further comprises an input/output device which is configured to receive information inputted by the user and output the information for the study and examination of the user, and the controller 320 may also generate the control signal according to the information inputted by the user. For instance, when the user hopes to acquire a certain health care operation, the user can directly input control information through the input unit without the sensing of the sensing components 311.

The head health care system provided by the embodiment of the present disclosure may be controlled by a remote electronic device communicated and connected with the head health care device, so that the user can examine his/her own head information at any time and any place by remote operation, and then health care operation can be performed, which is helpful for the user to control and use.

What are described above is related to the illustrative embodiments of the disclosure only and not limitative to the scope of the disclosure; the scopes of the disclosure are defined by the accompanying claims.

The application claims priority to the Chinese patent application No. 201510539739.4, filed Aug. 28, 2015, the entire disclosure of which is incorporated herein by reference as part of the present application.

What is claimed is:

1. A head health care device, comprising:
   a body;
   a plurality of sensing components provided and projected on an outer surface of the body, in which each sensing component is configured to sense head information of a user; and
   a plurality of health care components provided and projected on the outer surface of the body, in which the health care components are configured to perform health care operations on a head of the user according to a control signal;
   wherein the health care device is in a shape of a comb; and the sensing components and the health care components are disposed on comb teeth of the comb, and
   one health care component and one sensing component are disposed on a same comb tooth.

2. The health care device according to claim 1, wherein at least one sensing component includes a sensing signal output part; at least one sensing component includes a sensing signal receiving part;
   the sensing signal output part is configured to send out a sensing drive signal; and
   the sensing signal receiving part is configured to receive a sensing signal.

3. The health care device according to claim 2, wherein a number of the at least one sensing component including the sensing signal receiving part is greater than a number of the at least one sensing component including the sensing signal output part; and sensing components each including the sensing signal receiving part are distributed around the sensing components each including the sensing signal output part.

4. The health care device according to claim 2, wherein the health care device further comprises a controller; and
   the controller is disposed in the body and configured to generate the control signal according to information sensed by the sensing components, and send the control signal to the health care components to control the health care operations of the health care components, and
   the controller further includes a sensing signal transmitting terminal and a sensing signal receiving terminal;
   the sensing signal transmitting terminal is configured to provide the sensing drive signal to the sensing signal output part of the sensing component; and the sensing signal receiving terminal is configured to receive the sensing signal from the sensing signal receiving part of the sensing component.

5. The health care device according to claim 1, wherein the body is internally provided with a cavity with a limited space; the cavity is provided with a nutrient solution storage tank; and
   the nutrient solution storage tank is configured to output nutrient solution to the health care components according to the control signal and allow the nutrient solution to be discharged.

6. The health care device according to claim 5, wherein the nutrient solution storage tank includes a plurality of vessels;
   the vessels are respectively configured to store different types of nutrient solutions, and at least one type of nutrient solution in the vessels can be conveyed to one corresponding health care component according to an instruction of the control signal and discharged.

7. The health care device according to claim 5, wherein the health care device further comprises a nutrient solution storage tank driver; and
   the nutrient solution storage tank driver is configured to drive the nutrient solution storage tank to output the nutrient solution to the health care components according to the control signal.

8. The health care device according to claim 1, wherein the health care device further comprises a controller; and
   the controller is disposed in the body and configured to generate the control signal according to information sensed by the sensing components, and send the control signal to the health care components to control the health care operations of the health care components.

9. The health care device according to claim 1, wherein the health care device further comprises a vibrating component; and
   the vibrating component drives at least one health care component to vibrate according to the control signal.

10. The health care device according to claim 1, wherein the health care device further comprises an information storage device.

11. The health care device according to claim 1, wherein the health care device further comprises a signal transmitting/receiving device; and
    the signal transmitting/receiving device is configured to communicate with an external device and receive the control signal.

12. The health care device according to claim 1, wherein the health care device further comprises a plurality of function buttons.

13. The health care device according to claim 1, wherein the health care device further comprises a built-in power supply or a power port.

14. The health care device according to claim 1, wherein the health care device further comprises an input/output device.

15. A head health care system, comprising:
    the head health care device according to claim 1; and
    a controller configured to communicate with the head health care device,
    wherein the head health care device is configured to send the head information of the user sensed by the sensing components to the controller; and
    the controller is configured to generate the control signal according to the received head information of the user, and send the control signal to the health care components to control the health care operations of the health care components.

16. The system according to claim 15, wherein the controller further includes a sensing signal transmitting terminal and a sensing signal receiving terminal;
the sensing signal transmitting terminal is configured to provide the sensing drive signal to the sensing signal output part of the sensing component; and
the sensing signal receiving terminal is configured to receive the sensing signal from the sensing signal receiving part of the sensing component.

17. The system according to claim 15, wherein the system further comprises an input/output device;
the input/output device is configured to receive information inputted by the user; and
the controller also generates the control signal according to the information inputted by the user.

18. The system according to claim 15, wherein the controller is a mobile terminal configured to communicate with the head health care device.

* * * * *